(12) United States Patent
Reboni et al.

(10) Patent No.: US 8,686,369 B2
(45) Date of Patent: Apr. 1, 2014

(54) FLAT PANEL X-RAY DETECTOR AND METHOD FOR ITS MANUFACTURING

(75) Inventors: Vol'demar Osval'dovich Reboni, Sankt-Petersburg (RU); Yury Arnol'dovich Veip, Sankt-Petersburg (RU); Vitaly Valer'evich Jurenja, Pushkin (RU); Yury Gennad'evich Leont'ev, Sosnovyi Bor (RU)

(73) Assignee: Zakrytoe akcionernoe obshchestvo "Impul's", Sankt-Petersburg (RU)

( * ) Notice: Subject to any disclaimer, the term of this patent is extended or adjusted under 35 U.S.C. 154(b) by 166 days.

(21) Appl. No.: 13/447,768

(22) Filed: Apr. 16, 2012

(65) Prior Publication Data

US 2012/0261582 A1    Oct. 18, 2012

(30) Foreign Application Priority Data

Apr. 15, 2011    (RU) ................ 2011114783

(51) Int. Cl.
*G01T 1/20*    (2006.01)
(52) U.S. Cl.
CPC .................... *G01T 1/2018* (2013.01)
USPC ....................................................... 250/366
(58) Field of Classification Search
CPC ....... G01T 1/2018; G01T 1/2914; G01T 5/08; A61B 6/4283; A61B 6/4233; G06T 2207/10116
USPC ........................................................ 250/366
See application file for complete search history.

(56) References Cited

U.S. PATENT DOCUMENTS

| | | | |
|---|---|---|---|
| 5,464,984 A * | 11/1995 | Cox et al. ................. | 250/370.11 |
| 6,747,277 B2 | 6/2004 | Mori et al. | |
| 7,019,303 B2 | 3/2006 | Homme et al. | |
| 7,053,379 B2 * | 5/2006 | Watanabe ................ | 250/370.09 |
| 7,202,481 B2 * | 4/2007 | Spahn et al. ............. | 250/370.09 |
| 7,495,644 B2 * | 2/2009 | Hirakata ......................... | 345/92 |
| 2002/0158208 A1 * | 10/2002 | Mori et al. ................ | 250/370.11 |
| 2005/0056789 A1 * | 3/2005 | Spahn et al. ............. | 250/370.09 |
| 2005/0199816 A1 * | 9/2005 | Amemiya et al. ....... | 250/363.05 |
| 2008/0112535 A1 * | 5/2008 | Wojcik et al. ................ | 378/62 |

\* cited by examiner

*Primary Examiner* — Kiho Kim
(74) *Attorney, Agent, or Firm* — Patentbar International, P.C.

(57) ABSTRACT

The present invention relates to imaging devices. Technical solutions—creation of highly manufacturable assemblage of flat panel x-ray detectors, and providing high quality images. The flat panel x-ray detector comprises a light-blocking split housing consisting of a bottom and top parts; in the housing sequentially along the incident radiation pathway are installed an elastic radiotransparent layer, x-ray screen on the substrate and sensors being fastened to the mounting base. Sensors are fastened on the mounting base with a possibility to be removed with a possibility to be removed by means of additionally set on the sensor substrates intermediate elements. To fix the screen it is additionally introduced a bar inside which the edge of said screen substrate is fixed, and the bar is fastened to mounting base with a possibility to be removed.

11 Claims, 6 Drawing Sheets

FLAT PANEL X-RAY DETECTOR AND METHOD FOR ITS MANUFACTURING

RELATED APPLICATIONS

This application claims priority to Russian Patent Application No. RU 2011114783, filed Apr. 15, 2011, which is incorporated herein by reference in its entirety.

FIELD OF THE INVENTION

The present invention relates to an imaging device receiving an image carrying x-ray beam, and, more particularly, to a detector registering x-ray images having a panel of photosensitive sensors and also to receiver design technique. This detector may be applied within x-ray diagnostic apparatuses, mainly, for medical applications.

BACKGROUND OF THE INVENTION

In imaging devices by means of radiation e.g. x-rays, the object-target undergoes radiation exposure that passes through it and forms thus, an amplitude of radiation bearing image data. Further, it reaches the surface of the flat panel detector having a multi-layered structure. Radiation passes through a light-blocking layer of the above-mentioned detector and being converted into light in the converting layer it reaches the array of photosensitive elements that change their electric features due to the light incidence. This results in generating electric signal corresponding with radiation energy obtained by photosensitive elements. Output signals are provided for digital image acquisition.

It is known a flat panel detector and a method for its manufacturing (U.S. Pat. No. 7,019,303, published Mar. 28, 2006). In accordance with technical decision of the said patent the receiver contains the arranged along the pathway of incident radiation x-ray screen and an array of photosensitive elements that form a united photosensitive surface with necessary dimensions. Sensors being placed on a mounting base close to each other are adhered to it. An x-ray screen represents a luminescent layer spread over a light transmissive substrate. The x-ray screen is optically connected to an active area of photosensitive elements. Additionally, the luminescent layer of the x-ray screen may be sealed with transmissive to x-rays water-proof chemically stable protective film.

It is also known an x-ray detector and a method for its manufacturing (U.S. Pat. No. 6,747,277, published Aug. 8, 2004). Technical decisions and the method for manufacturing the detector disclosed in this patent are the closest to those claimed hereunder. The detector built as a multilevel structure located in the split housing comprises the x-ray screen arranged along the pathway of incident radiation and an array of photosensitive elements forming a united photosensitive surface of required size. The housing is made of light-blocking material. Sensors or photosensitive elements being placed on a mounting base close to each other are adhered to it. The x-ray screen being optically connected to an active area of photosensitive elements represents a luminescent layer spread over a light transmissive substrate that may be made of glass or any other material such as aluminum, amorphous carbon or beryllium; over the screen there is a bumping layer to press the screen to the photosensitive element surface.

Common drawback of described devices and methods for their manufacturing is poor manufacturability that results in artifacts and image quality reducing. Also, when manufacturing said constructions it is difficult to provide prescribed accuracy of detector elements positioning, particularly, of sensors on the mounting base; as a result there may appear geometric roughnesses difference in height of the common surface of the photosensitive detector surface consisting of photosensitive surfaces of several sensors. U.S. Pat. No. 6,747,277, for example, disclosed a more complicated housing construction for screen mounting and fastening by means of introduction of supplemented locating fixture: over the side perimeter of the housing wall there is a flange on which a locating fixture to limit the horizontal screen shift against of photosensitive surface is mounted. As the screen substrate is hard it is not possible to provide total contact of the whole screen surface with the whole photosensitive element surface that thus, results in additional artifacts emerging and therefore, image quality reduction. Besides, described constructions don't provide sensor interchangeability because of sensor and mounting base connection being executed with the use of glue the replacement of some failed elements becomes practically impossible.

SUMMARY OF THE INVENTION

A flat panel x-ray detector used in imaging devices where a target-object is exposed to x-rays that pass through it and thus, form an image-carrying beam of x-rays and further, x-rays are projected onto the flat panel x-ray detector surface having a multi-layered structure. Radiation passes through a light-blocking layer of said detector and being converted into light in the converting layer it reaches the array of photosensitive elements that change their electric features due to the light incidence.

Output signals are provided for digital image acquisition.

There is a necessity in improved construction and manufacturing method which would offer high manufacturability at flat panel x-ray detector development without image quality reducing.

In the claimed group of inventions it is achieved the following comprehensive technical result:
  simplification of detector assembly process providing high positional location accuracy of detector elements,
  possibility of failed single photosensitive element replacement that excludes the necessity of disposal of the whole plane with mounted sensors,
  possibility to produce a flat panel x-ray detector with different amount of photosensitive elements (more than four),
  reduction of the influence of photosensitive surface height difference appearing at the assemblage stage because of poor photosensitive element density as well as a level difference at photosensitive element butting on x-ray image quality.

Indicated comprehensive technical result has been achieved by the use of the claimed group of inventions that form an integrated conception of invention, and represent a flat panel x-ray detector and a method for its manufacturing.

Indicated comprehensive technical result has been achieved in the claimed flat panel x-ray detector (hereinafter 'detector'), comprising a light-blocking split housing consisting of a bottom and top parts; and in said housing sequentially along the incident radiation pathway are mounted an elastic radiotransparent layer, x-ray screen on the substrate and sensors fastened on the mounting base, each of which has a photosensitive surface exposed to the incident radiation, and a bottom, and provided with electrical wires on one of the side walls.

Main distinctive features of the claimed detector are as follows: sensors are fastened to the mounting base with the possibility to be removed due to supplementary installed on sensors substrates intermediate elements; for screen fastening there was introduced a bar, inside which the edge of said screen substrate is fixed, and the bar with the fixed inside it edge of said screen substrate is fastened to the mounting base with the possibility to be removed.

Additional distinctive features of the claimed detector are as follows: at developing the detector the following structural features may be used:

- at least one intermediate element is fastened on the sensor substrate with the use of detachable connection;
- the surface of the mounting base contains mounting sockets to install intermediate elements, and said elements have seating lugs;
- said bar includes at least two openings that are aligned at least with two corresponding seating lugs located on the mounting base;
- the screen's substrate is flexible;
- seating lugs look like guide pins the pilot portion of which has a conic side surface, the guide pins are spring-loaded and located in mounting base cavities;
- sensors are located on two or more levels against each other, and sensors downwards there is an intermediate space comprising at least one fiber-optic plate.

Indicated comprehensive technical result has been achieved in the claimed method for manufacturing the flat panel x-ray detector comprising a light-blocking split housing consisting of a bottom and top parts; and in said housing sequentially along the incident radiation pathway are mounted an elastic radiotransparent layer, x-ray screen on the substrate and sensors fastened on the mounting base, each of which has a photosensitive surface exposed to the incident radiation, and a bottom, and provided with electrical wires on one of the side walls.

Main distinctive features of the claimed method are as follows: on each sensor substrate is fastened an intermediate element providing removable connection between the sensor's substrate and mounting base; the screen represents a phosphor layer spread over a flexible substrate, for screen fastening there was introduced a bar, inside which the edge of said screen substrate is fixed, and said bar is fastened on the mounting base with the possibility to be removed, and the bar fastening process is executed, in essence, while the bar having horizontal position, and, in essence, while the surfaces of screen and mounting base with the fixed on it sensors having vertical position.

Additional distinctive features of the claimed method are as follows:

- at least one intermediate element is fastened on the sensor substrate with the use of detachable connection;
- the screen phosphor layer and sensor photosensitive surfaces are coupled forming a single profile by means of pressure distribution on the screen surface with the use of said elastic layer.

Main distinctive features of the claimed group of inventions allow providing advantages over known technical solutions in the following manner. Sensors are fastened on the mounting base with the possibility to be removed due to supplementary installed on said sensors substrates intermediate elements with the use of detachable connection. This allows replacement of failed sensors excluding the whole mounting base with sensors disposal, and moreover, simplifies sensors installation and increases their positioning accuracy on the mounting base.

Presence of screen fastening element such as a bar with some openings suggests a more simple installation process of the x-ray screen inside the detector surface and its higher positioning accuracy.

While positioning sensors on the mounting base, it is inevitable to appear difference in height (geometrical nonuniformity) of photosensitive surface. Also there is geometrical nonuniformity of photosensitive surface of each sensor. The fact that the screen substrate is flexible allows minimizing negative impact of the difference in height and geometrical nonuniformity of sensor photosensitive surface on x-ray image quality. It is achieved by coupling the screen phosphor layer and sensor photosensitive surface that form a common profile by means of pressure distribution on the flexible screen substrate with the use of said elastic layer.

The intermediate layer may be made of plastic or metal, and being of a rectangular shape or, for example, of flat profile frame having a closed-form in a cross-section. Its shape may match the sensor substrate shape. The intermediate layer may be fastened to the sensor substrate with the use of detachable connection. The use of the intermediate layer considerably simplifies the replacement of failed photosensitive elements. This is due to putting glue not over the whole sensor substrate area but only on the part of the intermediate layer to fix it on the mounting base in a required position not for fastening. The fastening to the mounting base is executed with the use of detachable connection.

To reduce the weight of the mounting base some cavities corresponding to sensor number used are provided.

A screen fastening element may be a rigid bar with two openings aligned along said bar, and said openings are coupled with, at least two corresponding supporting pins located on the mounting base correspondingly. Said fastening element execution provides simple and exact installation of the screen in the detector surface and its easy and hard fastening to the mounting base.

The use of intermediate elements for photosensitive elements and a bar for the screen fastening suggests a rather easier detector assembling process, and disposition of the photosensitive elements on different levels as well as the use of fiber-optic plates provides the development of flat panel detectors of any dimensions without using complex technology of photosensitive element pinouts.

BRIEF DESCRIPTION OF THE DRAWINGS

The accompanying drawings, which are incorporated in and form a part of this specification, illustrate embodiments of the invention and, together with the description, serve to explain the principles of the invention. In the drawings:

FIG. 2 shows flat panel x-ray detector:
1—a lower part of the detector housing,
2—a basket frame,
3—an upper part of the detector housing,
4—a mounting base,
5—a sensor,
7—a phosphor screen,
8—elastic layer transparent to x-rays,
15—supporting lugs on the mounting base 4,
20—seating (shown not all openings),
21—seating lugs,
22—incident x-rays.

DETAILED DESCRIPTION OF THE INVENTION

One of the best embodiments of the present invention is described below.

Figure 1:
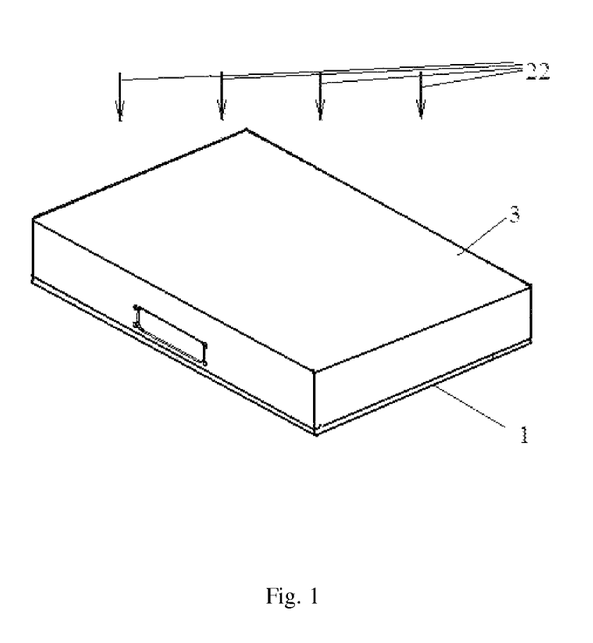
FIG. 1 shows detector assembly:
1—a lower part of the detector housing,
3—an upper part of the detector housing,
22—incident x-rays.

FIG. 1 shows a detector assembly. The housing of the x-ray detector being a rectangular parallelepiped consists of a lower part 1 and an upper part 3. The upper part is performed as a cover being exposed to incident x-rays 22, and the lower part is as a flat base.

Figure 2:
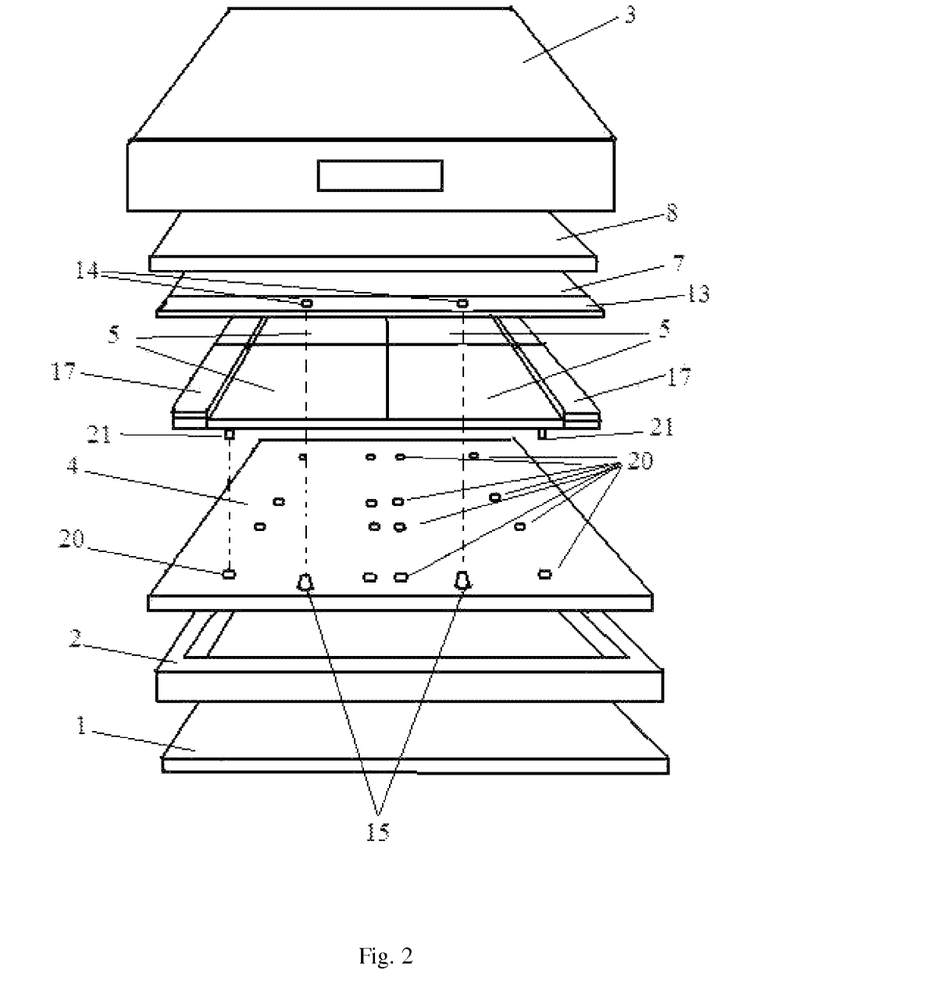
Figure 3:
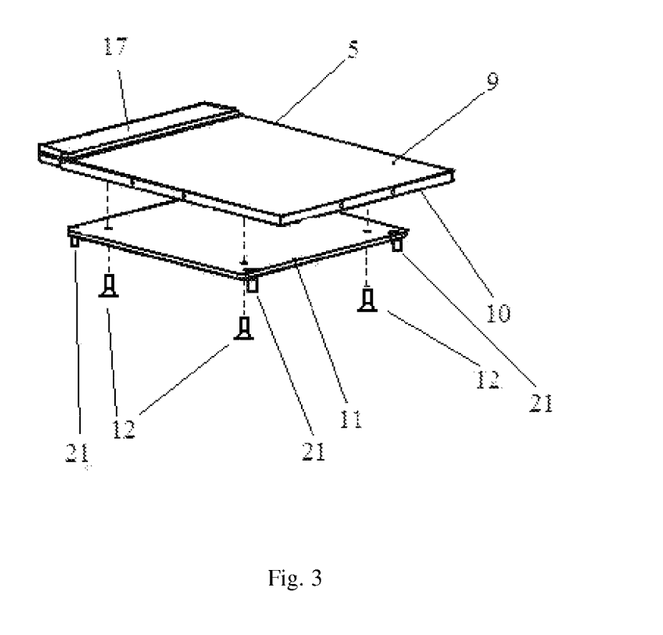
FIG. 3 shows a sensor and an intermediate element:
5—a sensor,
9—a photosensitive surface of the sensor 5,
10—the substrate of the sensor 5,
11—an intermediate element, 12—fastening screws,
21—seating lugs.
Figure 4:
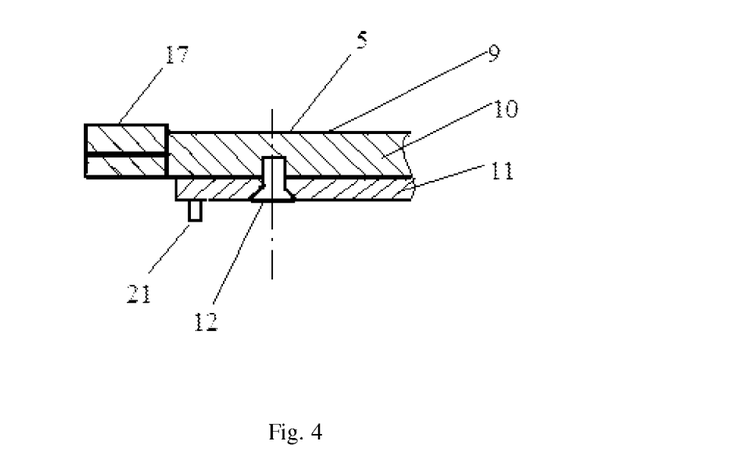
FIG. 4 shows the coupling of intermediate element with the sensor substrate in a section:
5—a sensor,
9—a photosensitive surface of the sensor 5,
10—the substrate of the sensor 5,
11—an intermediate element,
12—a fastening screw,
21—a seating lug.

A layout of the detector is shown in FIG. 2. The detector comprises the following main units: a split housing, inside which portions of detector are placed, and consisting of the lower part 1 and the upper part 3. On the lower part 1 is installed a basket frame 2. On the basket frame 2 is installed a mounting base 4, on which are installed sensors 5. Sensors 5 are intended to receive radiation of the visible-light spectrum coming from a phosphor screen 7, and to convert this radiation into electrical signals, which are put out from electrical pins of sensors 5 onto a monitor display (not shown) aiming at electrical signal-based image acquisition. The mounting base 4 may have some cavities (not shown), with the aim of reducing mounting base weight. Sensors 5 being disposed on the mounting base 4 in immediate proximity to each other, form practically continuous photosensitive surface. The size of the photosensitive surface should not be smaller than the object cross-section area being under x-ray examination. There is a screen on the photosensitive surface. The screen 7 is of sensitive phosphor layer spread over a substrate. In the phosphor layer incident x-rays is converted into visible radiation that reaches sensor photosensitive surface. In between the screen 7 and inner surface of the upper housing part 3 is located elastic layer 8 transparent to the x-rays. The screen 7 may be sealed with transmissive to x-rays water-proof chemically stable protective film. The luminescent layer of the x-ray screen 7 and the photosensitive sensor surface are coupled forming a single profile by means of pressure distribution on the screen surface with the use of said elastic layer 8 made out of photosensitive sensor surfaces being installed on the mounting base FIGS. 3 and 4 show one of the sensors 5 and the intermediate element 11. Each sensor 5 (FIG. 3) has a photosensitive surface 9 and a substrate 10. The photosensitive surface 9 is made by spreading some photosensitive material over special substrates (not shown in FIG. 3), that are fastened to the substrate 10. To the substrate 10 by means of threaded connection (fastening screws 12) is fixed the intermediate element 11, that may be performed, for instance, as a square or a flat profile frame. Fastening screws 12, by means of which the intermediate element 11 is connected to the substrate 10, are flush-mounted against the intermediate element surface.

One edge of the screen substrate 7 (FIG. 7) is fastened to an end of the bar 13 with the openings 14, intended for disposing inside them supporting pins 15, performed in the mounting base 4 correspondingly.

Figure 7:
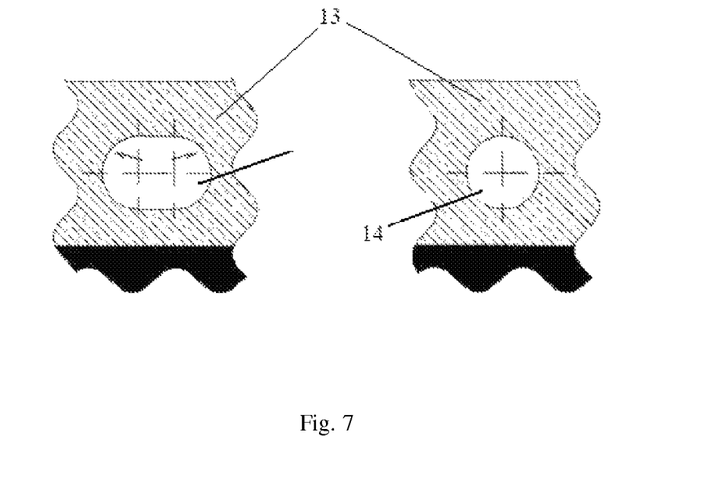
FIG. 7 shows a "what-if" embodiment of openings 14, performed in the bar 13 to fasten the screen 7.

FIG. 7 shows a "what-if" embodiment of openings 14, performed in the bar 13 to fasten the screen. The openings 14 in the bar 13 are performed in a way to simplify the x-ray screen installation procedure, and to install it hard and without any shift in the plane parallel to the photosensitive surface 9. One of the openings 14 is circle-shaped, and another one has a form of an ellipse. Such performance of the openings 14 provides an accurate positioning of the screen 7 and allows avoiding undesirable tensions in the assembled detector because of temperature drop of the detector itself and of the environment.

Figure 9:
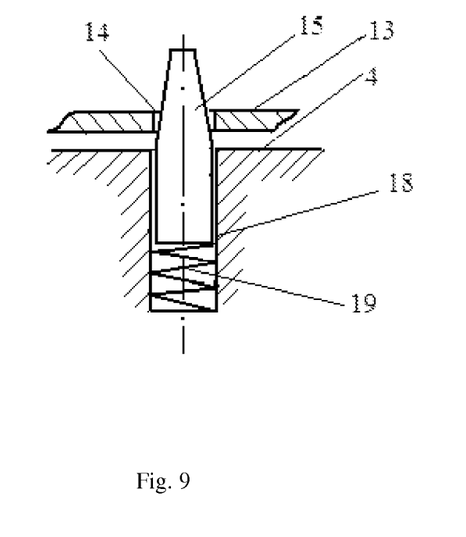
FIG. 9 shows one of the supporting lugs 15, performed in the mounting base 4 in the form of supporting pins and intended for installation of the bar 13 of the screen 7:
4—a mounting base,
15—supporting pins in the mounting base 4,
18—a cavity,
19—a spring.

For the accurate positioning of the screen 7 the bar 13 is installed on the mounting base 4 with the use of supporting pins 15, the guide pins of which (FIG. 9) have conic side surfaces, the guide pins are spring-loaded (spring 19), and located in the mounting base cavities 18.

Figure 8:
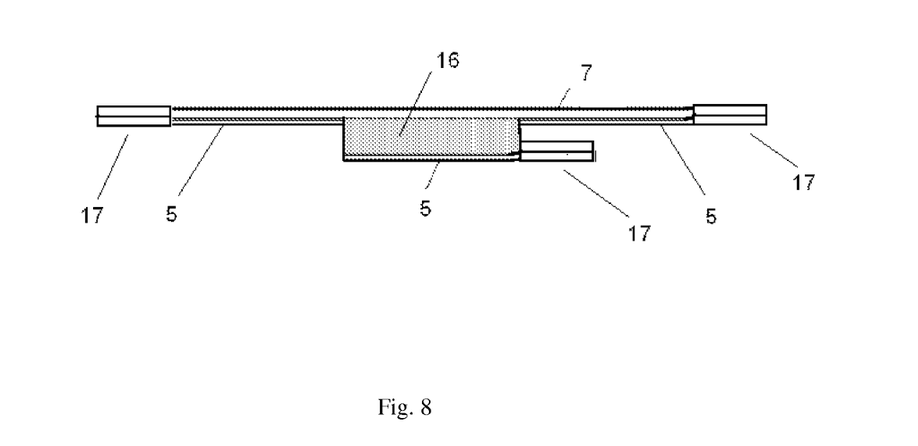
FIG. 8 shows one of "what-if" embodiments of two-level sensor disposition using fiber-optic plates:
5—a sensor,
7—a phosphor screen,
16—a fiber-optic plate,
17—sensor pinouts.

When being 2 or 4 sensors are located within one plane, and therefore, photosensitive surfaces are located within one plane as well. Sensors 5 are butted a minimal gap providing required thermal expansion and image continuity. FIG. 8 shows one of "what-if" ways to form a single photosensitive surface with a number of sensors more than 4. Since the sensor pins are located on one of the side walls, so when there are 4 sensors they can not be placed in one level in immediate proximity to each other to build a continuous photosensitive surface. In this case sensors 5 are placed in two levels. The first level is that one located first along the pathway of incident radiation and the second level follows it respectively. Sensors 5 of the first level and those of the second one are placed in such a way to build virtually a continuous photosensitive surface of required dimensions. By that, the first and the second levels in the direction perpendicular to the photosensitive surface are separated to form an intermediate space intended for placing the fiber-optic plate 16 on the photosensitive surface of the second level.

A flat panel x-ray detector is performed in accordance to the method claimed hereunder as follows.

In the light-blocking split housing consisting of a bottom and top parts sequentially along the incident radiation pathway is mounted an elastic radiotransparent layer 8, and x-ray screen on the substrate and sensors fastened on the mounting base 4, each of which having a photosensitive surface 9 exposed to the incident radiation, and a plane-parallel basement 10, and provided with electrical wires 17 on one of the side walls.

To the bottom part 1 of the detector housing, made, for instance, of lead, is fastened to a basket frame 2, on which said mounting base 4 is installed. On the mounting base there are some seatings 20 (FIG. 2), which serve for positioning sensors 5. They have seating lugs 21 (FIG. 2, 3, 4), performed in the intermediate element 11, being fastened to the sensor substrate 10.

The x-ray screen 7 represents a continuous over the light-blocking radiotransparent substrate scintillating layer, converting x-ray energy into light energy of a visible-light spectrum and, being optically coupled with sensor photosensitive surface. When installing the x-ray screen 7 it is used the bar 13 inside which the edge of the substrate of the screen 7 is fastened. Said bar 13 is fastened on the mounting base 4 with a possibility to be removed. The screen substrate may be flexible. In such a case the fastening procedure is executed with the bar being in horizontal position and, the screen 7 and sensor photosensitive surface being in vertical position. These planes being installed parallel to each other are juxtaposed to the entire contact. Such an installation procedure, notably, with the vertical positioning of said planes allows the flexible screen not to be disturbed during the above procedure.

Figure 5:
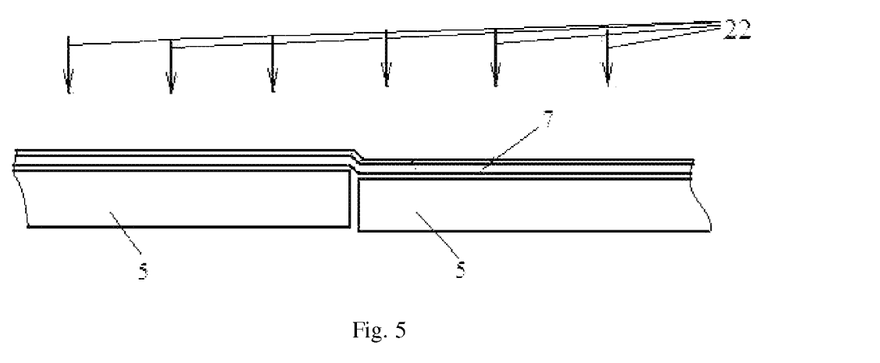
FIG. 5 shows a level difference in photosensitive sensor butting areas:
5—a sensor,
7—a phosphor screen,
22—incident x-rays.
Figure 6:
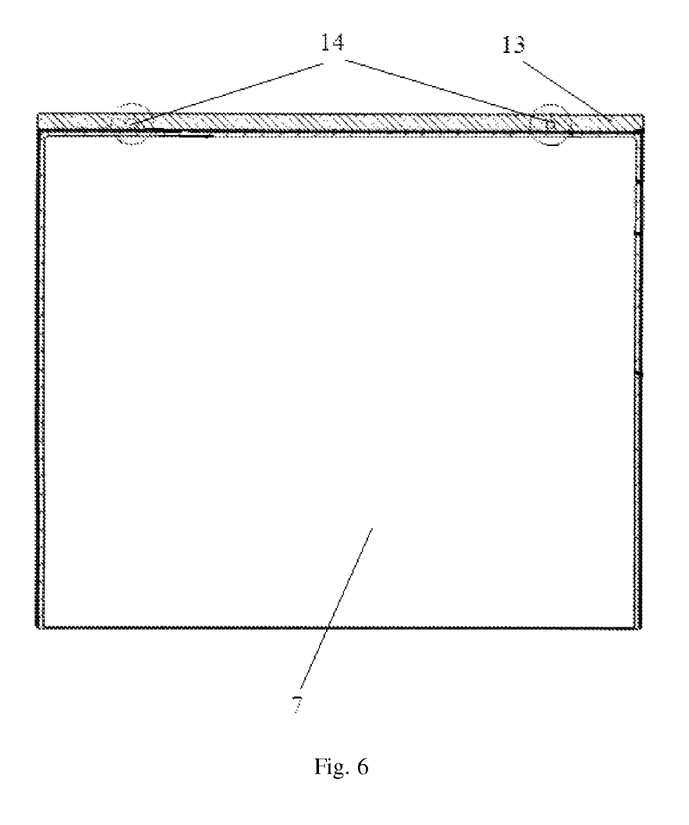
FIG. 6 shows a screen:
7—a phosphor screen,
13—a bar,
14—openings in the bar 13.

The screen phosphor layer and sensor photosensitive surface is coupled forming a common profile by means of pressure distribution on the flexible screen substrate with the use of said elastic layer, for example, foam polyurethane sheet material placed between the screen and the top part 3 of the housing. As shown in FIG. 5, one of the reasons to occur inequalities in common sensor photosensitive surface is impossibility to get a perfectly accurate sensor butting. Elastic layer provides uniform pressure distribution over the screen surface 7 and, its flexible substrate proves to be distorted in such a way that the joining point of the screen 7, and of sensor photosensitive surface form a common profile. The screen substrate thickness is selected to be 0.25 mm, for example, aluminum foil, that is covered with phosphor layer (may be used CsI, thickness 0.2 mm)

While assembling detector with sensors according to the scheme for example, 3×3 there occurs a problem to install a central sensor 5 because of pinouts 17 being located on one of its side walls (FIG. 8). To solve said problem sensors 5 are located on different levels of the detector height. The first level is that one located first along the pathway of incident radiation and the second level follows it respectively etc. FIG. 8 shows a two-level structure. By that, the first and the second levels in the direction perpendicular to the photosensitive surface are separated to form an intermediate space intended for placing the fiber-optic plate on the photosensitive surface of the second level. Sensors of the first and second levels are juxtaposed to form a united photosensitive surface of required size. Sensors may be located in the planes being on several levels between which there should be an intermediate space comprising at least one fiber-optic plate.

INDUSTRIAL APPLICABILITY

The detector produced under the method claimed is used within the x-ray equipment to diagnose objects. X-ray beams produced by an x-ray source and passing consequently through an object being under examination, top part 3 of the radiotransparent housing, elastic layer 8, x-ray screen 7, converting x-ray energy into visible energy, reach photosensitive surface 9 of sensors 5, and being converted into electric digital signal that through electric outputs 17 arrive on the appropriate inputs of a digital signal into visible image converter (not shown in figures). It is reasonable to use CMOS "Active-Pixel Sensor" as sensors. Each of such sensors comprises a photosensitive surface generated in a semi-conducting substrate that is fixed on the sensor base. Sensors have plane-parallel bases with electric pinouts located on one of its side walls.

Therefore, technical solutions for the detector and method of its production provide creation of highly manufacturable flat panel x-ray detectors, comprising sufficient number of photosensitive elements without complicated pinout technique; decreased requirements to difference in height and geometrical nonuniformity of photosensitive surface, considerably decreasing artifacts in images and increasing their quality thereby; replacement failed single sensors, excluding the necessity of disposal of the whole circuit board comprising sensors.

What is claimed is:

1. A flat panel x-ray detector comprising:
   a light-blocking split housing having of a bottom and top parts;
   an elastic radiotransparent layer, a x-ray screen on a substrate and sensors disposed sequentially in said housing along an optical path of incident radiation, fastened to a mounting base;
   each of the sensors having a photosensitive surface exposed to the incident radiation, a base substrate and electric pinouts located on one of its side walls; and
   a bar for fastening the x-ray screen at an end of the bar, the bar being removably fastened to the mounting base;
   wherein the sensors are removably fastened on the mounting base and wherein the sensors can be removed by way of intermediate elements.

2. The detector of claim 1, wherein, at least one intermediate element is fixed on the sensor substrate with the use of a detachable element.

3. The detector of claim 2, wherein a surface of the mounting base comprises seatings to install intermediate elements, and said elements comprise seating lugs matching appropriate seatings.

4. The detector of claim 3, wherein said bar is made with at least two openings, and the at least two openings are coupled with at least two corresponding lugs disposed on the mounting base.

5. The detector of claim 4, wherein the screen substrate is flexible.

6. The detector of claim 5, wherein the seating lugs are made as guide pins having a conically shaped side surface of their pilot portion, the guide pins being spring-loaded and located in cavities of the mountain base.

7. The detector of claim 4, wherein the seating lugs are made as guide pins having a conically shaped side surface of their pilot portion, the guide pins being spring-loaded and located in cavities of the mountain base.

8. The detector of claim 1, wherein the sensors are located on two or more levels relative to each other, wherein at least one fiber-optic plate is disposed in an intermediate space formed between two or more levels.

9. A method of producing a flat panel x-ray detector, comprising:
   providing a light-blocking split housing comprising a bottom and top parts;
   sequentially disposed in said housing along an optical path of incident radiation an elastic radiotransparent layer, an x-ray screen on a substrate and sensors being fastened to a mounting base, each of the sensors having a photosensitive surface exposed to the incident radiation, a base substrate and electric pinouts located on one of side walls the sensors; and fastening the x-ray screen on a bar at an end of the bar the bar being removably fastened to the mounting base;

wherein the sensors are removably fastened on the mounting base and wherein the sensors can be removed by way of intermediate elements, and wherein the x-ray screen comprises a luminescent layer spread over a flexible substrate, and wherein removably fastening the x-ray screen occurs when the bar is in a horizontal position and surfaces of the screen and a surface of the mounting base with the fastened sensors are in a vertical position.

10. The method of claim 9, further comprising fastening at least one intermediate element at the base substrate by means of a detachable element.

11. The method of claim 10, further comprising coupling the luminescent layer of the x-ray screen and photosensitive sensor surfaces to form a common profile over the screen surface by means of said elastic layer.

* * * * *